United States Patent
Bannister

(10) Patent No.: US 8,435,196 B2
(45) Date of Patent: May 7, 2013

(54) ADJUSTABLE CLOSURE SYSTEM FOR AN ORTHOTIC DEVICE AND RELATED METHODS

(75) Inventor: Ed Bannister, Riverside, CA (US)

(73) Assignee: Bio Cybernetics International, Inc., La Verne, CA (US)

( * ) Notice: Subject to any disclaimer, the term of this patent is extended or adjusted under 35 U.S.C. 154(b) by 363 days.

(21) Appl. No.: 12/759,396

(22) Filed: Apr. 13, 2010

(65) Prior Publication Data

US 2010/0268141 A1    Oct. 21, 2010

Related U.S. Application Data

(60) Provisional application No. 61/168,748, filed on Apr. 13, 2009.

(51) Int. Cl.
*A61F 5/00* (2006.01)

(52) U.S. Cl.
USPC ............................................................ 602/19

(58) Field of Classification Search .............. 602/19; 128/869, 870, 876; 383/74; 191/12 R; 2/44, 2/45, 336, 337, 338, 339, 341, 269; 24/31 R, 24/32, 68 R, 69 ST, 712, 712.1, 712.9, 713, 24/18, 68 F, 129 R, 910; 450/2
See application file for complete search history.

(56) References Cited

U.S. PATENT DOCUMENTS

| | | | |
|---|---|---|---|
| 3,927,655 A | 12/1975 | Wax | |
| 4,508,110 A * | 4/1985 | Modglin | 602/19 |
| 4,677,699 A | 7/1987 | Barabe | |
| 5,158,098 A * | 10/1992 | Jalalian | 128/876 |
| 5,421,809 A | 6/1995 | Rise | |
| 5,690,609 A | 11/1997 | Heinz | |
| 5,803,086 A * | 9/1998 | Scholz et al. | 128/849 |
| RE35,940 E | 10/1998 | Heinz et al. | |
| 6,213,968 B1 | 4/2001 | Heinz et al. | |
| 6,317,894 B1 * | 11/2001 | Blechman | 2/269 |
| 6,389,620 B1 * | 5/2002 | Hennessy | 5/120 |
| 7,001,348 B2 | 2/2006 | Garth et al. | |
| 7,201,727 B2 | 4/2007 | Schwenn et al. | |
| 7,210,605 B2 * | 5/2007 | Willows et al. | 224/637 |
| 2002/0008125 A1 * | 1/2002 | Caputi | 224/257 |
| 2005/0267390 A1 * | 12/2005 | Garth et al. | 602/19 |
| 2010/0038199 A1 * | 2/2010 | Wengreen | 191/12 R |

* cited by examiner

*Primary Examiner* — Patricia Bianco
*Assistant Examiner* — Raymond E Harris
(74) *Attorney, Agent, or Firm* — Holland & Hart LLP

(57) ABSTRACT

Described herein is a closure system and methods for adjusting an orthotic device. The closure system can include a handle element, a take-up element configured to be removably received by the handle element, and a cord having a length and secured at one end to the take-up element and at an opposite end to the orthotic device to facilitate adjustment of the orthotic device. The take-up element is configured to adjust the usable length of the cord. Also described herein is a back brace apparatus having a take-up element.

14 Claims, 5 Drawing Sheets

ADJUSTABLE CLOSURE SYSTEM FOR AN ORTHOTIC DEVICE AND RELATED METHODS

CROSS-REFERENCE TO RELATED APPLICATION

The present application claims priority to U.S. Provisional Application No. 61/168,748, entitled "Adjustable Closure System for an Orthotic Device and Related Methods," filed Apr. 13, 2009, the entire contents of which are herein incorporated by reference.

BACKGROUND OF THE INVENTION

The present invention generally relates to a closure system and methods for an orthotic device, and more particularly to an orthotic device closure system having a take-up element for adjusting a cord length within the closure system.

An orthotic device or orthosis (commonly known as a brace or splint) is an orthopedic device that is typically applied to the limb or body. Among other things, the purpose can be to provide support, protection, pain reduction and/or replacement of lost function.

In this regard, a common method of alleviating pain in people suffering from back pain or injuries and promoting healing in post-operative back surgery patients is to stabilize the spine by means of an orthosis, such as a brace. There are a large variety of braces available depending on the diagnosis and physical needs of the individual. These devices include a multitude of construction materials and designs which can be snugly fitted around the patient's trunk and peripheral area such as the cervical and pelvic regions.

Such braces are effective in achieving spinal stability if worn properly and consistently. However, most patients have difficulty in manually adjusting the brace to fit tightly enough to provide adequate support and stability. This is especially true in the case of post-operative patients who are generally in pain and frequently lack sufficient strength to make the necessary adjustments.

U.S. Pat. No. 6,213,968, issued on Apr. 10, 2001 to Heinz et al. and assigned to BioCybemetics International of La Verne, Calif., describes a custom-fitted orthotic device which includes a pulley system that provides a mechanical advantage so as to require a minimal effort on the part or the patient when tightening the orthotic device around the torso, resulting in greater case of donning and doffing the device, ease of adjusting the device, comfort to the wearer of the device, and therefore greater patient compliance. The contents of this patent are hereby incorporated by reference in their entirety.

Although generally well suited for its intended purpose, further refinement of the Heinz et al. device, such as providing an improved closure system and methods for an orthotic device, is desirable. The present invention satisfies this and other needs, and provides further related advantages.

SUMMARY OF THE INVENTION

For purposes of summarizing the disclosure, exemplary embodiments of a closure system and methods for an orthotic device have been described herein.

The present invention is embodied in closure system for adjusting an orthotic device. In one embodiment, the closure system comprises a handle element having a pocket, a take-up element configured to be removably received into the pocket, and a cord having a length and secured at one end to the take-up element and at an opposite end to the orthotic device to facilitate adjustment of the orthotic device. The take-up element is configured to adjust the usable length of the cord.

In one embodiment, the take-up element is configured to adjust the usable length of the cord by receiving a segment of the cord. The take-up element can be configured to permit the segment of the cord to be wrapped around the take-up element. The take-up element can include a first recess and a second recess positioned at opposite ends of the take-up element for securely receiving a wrapped segment of the cord.

In another embodiment, the take-up element has a first orifice and a second orifice formed thereon. The cord extends through the first orifice and the second orifice to secure the cord to the take-up element.

In a further embodiment, the pocket is open at a first end for removably receiving the take-up element and substantially closed at a second end. The second end includes two holes, one sized and configured to permit the cord to enter the pocket, and the other sized and configured to permit the cord to exit the pocket.

The present invention is also embodied in a method for adjusting an orthotic device. In one embodiment, the method comprises the steps of securing a cord at one end to a take-up element and at an opposite end to the orthotic device to facilitate adjustment of the orthotic device, the cord having a length; and adjusting the usable length of the cord using the take-up element.

In one embodiment, the adjusting step includes the step of wrapping a segment of the cord around the take-up element. In another embodiment, the adjusting step includes the step of unwrapping a segment of the cord from around the take-up element. The method may further comprise the step of placing the take-up element into a pocket formed in a handle element attached to the cord.

The present invention is additionally embodied in a closure system for adjusting an orthotic device, the closure system comprising a handle element, a take-up element configured to be removably received by the handle element, and a cord having a length and secured at one end to the take-up element and at an opposite end to the orthotic device to facilitate adjustment of the orthotic device. The take-up element is configured to adjust the usable length of the cord.

The present invention is further embodied in a back brace apparatus. In one embodiment, the apparatus comprises a brace body adapted to be wrapped around the trunk of a patient, said brace body comprising two separate segments; means at the end of each brace segment for allowing the two ends to be detachably connected together around the patient's trunk; a cable operatively connected to said two segments; a set of pulleys mounted on each brace segment with the cable running through a pulley on each segment in alteration, shortening of the cable pulling the two segments together and tightening the brace apparatus with the aid of a mechanical advantage dependent upon the number of pulleys mounted on each brace segment; and a take-up element received on the cable. The take-up element is configured to adjust a usable length of the cable.

In one embodiment, the back brace apparatus further comprises a pair of plates, said plates being detachably mounted on said segments, said set of pulleys being mounted on said plates.

These and other features and advantages of the present invention will be more readily apparent from the detailed description of the embodiments set forth below taken in conjunction with the accompanying drawings.

BRIEF DESCRIPTION OF THE DRAWINGS

Embodiments of the present invention will now be described, by way of example only, with reference to the following drawings.

Figure 1:
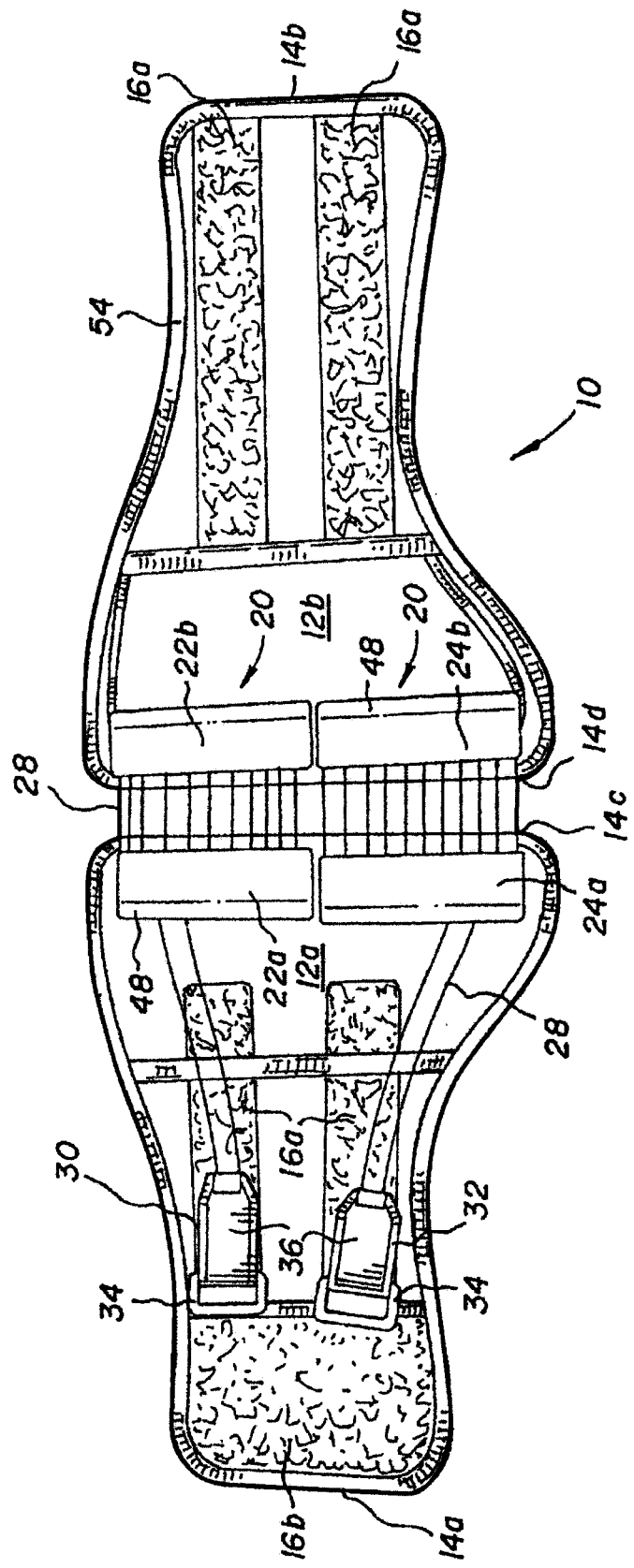
FIG. 1 is plan view of an example of an orthotic device having a closure system in accordance with an embodiment of the present invention.

Exemplary embodiments and their advantages are best understood by referring to the detailed description that follows. It should be appreciated that like reference numerals are used to identify like elements illustrated in one or more of the figures, wherein showings therein are for purposes of illustrating exemplary embodiments and not for purposes of limiting the same.

DETAILED DESCRIPTION OF THE PREFERRED EMBODIMENTS

For case of explaining various features of the closure system and methods described herein, the closure system and methods are described as they may relate to an orthotic device such as a back brace having a dual closure system. Persons of ordinary skill in the art will understand that the scope of the present disclosure is not intended to be limited to a back brace or to a dual closure system, but instead is intended to include a variety of body braces and/or orthotic devices having one or more closure systems.

Figure 2:
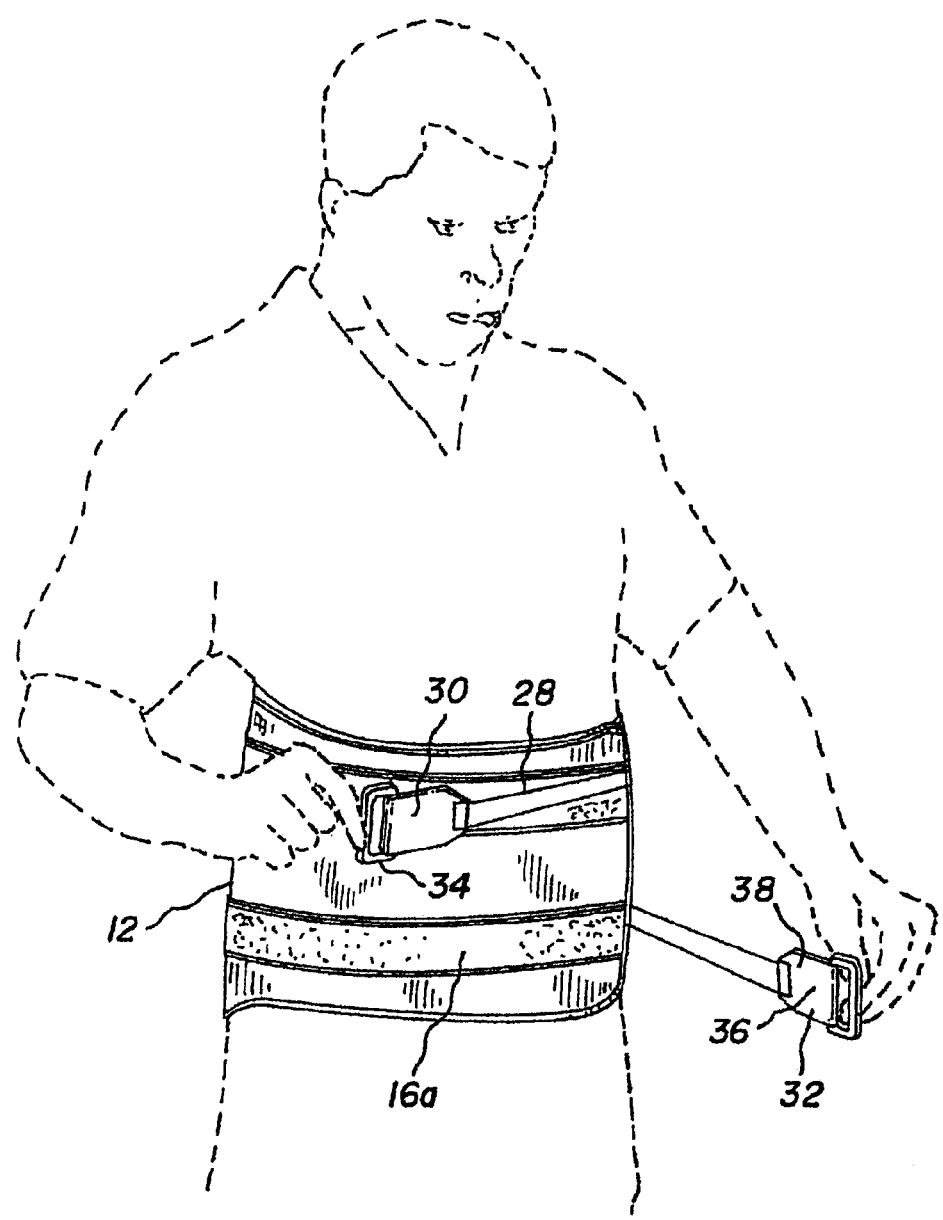
FIG. 2 shows the orthotic device of FIG. 1 being adjusted with the closure system, in accordance with an embodiment of the present invention.

As generally indicated in U.S. Pat. No. 6,213,968 to Heinz et al., many braces include one or more adjustment means to facilitate proper fit of the brace for support of a particular body part. Further disclosed in Heinz et al. and shown in FIG. 1 is an example of one such orthotic device that includes an orthosis or brace body 10 adapted to be wrapped around the torso or trunk of a user, the brace body including at least two segments 12a, 12b. fasteners 16a, 16b are provided at the distal or outer ends 14a, 14b of the segments of the brace body 12 to detachably secure the outer ends 14a, 14b around a user's torso. The orthotic device 10 includes a closure system having at least two cables/cords 28, each operatively connected to the at least two segments t12a, 12b. The closure system further includes at least two independent sets of pulley banks 22a, 22b, each set mounted on adjacent sides of opposing segments 12a, 12b with a cord 28 running through a corresponding pulley 26 on each adjacent segment 12a, 12b in series and in alteration, such that shortening each cord 28 will pull adjacent inner ends 14c, 14d together and tighten the body brace 12 around the user's torso, as shown in FIG. 2, with the aid of a mechanical advantage dependent upon the number of pulleys mounted on each brace segment.

More specifically, the brace body 10 illustrated in FIG. 1 may include two body brace segments 12a and 12b, each including apart of the individual adjuster or tightening means of the orthotic device closure system, disclosed herein. On opposite overlapping sides of opposite distal or free ends 14a and 14b of each brace body segment 12a, 12b are provided complementary fastener or fastening means 16a, 16b for securing the two free ends 14a and 14b together after the brace is wrapped around the patient's torso. Although buttons and button holes, snap fasteners, or other similar fasteners commonly used in garments may be employed to secure the free ends 14a, 14b of the brace body 10 together, much preferred are complementary sections of hook-and-loop fastener fabric mounted on opposite overlapping sides of opposite body brace segments 12a and 12b proximate at least the free ends 14a, 14b thereof. As shown in FIG. 1, complementary portions of hook-and-loop fabric are represented by fasteners 16a and 16b. Such material allows the free ends 14a and 14b to be removably attached to one another in a variety of positions. In addition to providing such complementary portions of hook-and-loop material at the free ends 14a and 14b of the brace body segments 12a and 12b, respectively, horizontal strips 16a of hook-and-loop material are arranged on the exterior surface of each brace body segment 12a, 12b to allow for removably securing handle elements 30, 32 attached to the ends of each cord 28 and used in the individual tension adjusters of the closure system.

Tension adjusters of the closure system used to custom fit the orthotic device 10, and generally described above, include at least two independent pulley sets 20. Each set of pulleys includes a pair of opposing banks of pulleys (an upper set including banks 22a and 22b and a lower set including banks 24a and 24b). Each bank includes a plurality of individual pulleys 26 (FIG. 5) and a corresponding cord 28 looped serially and in alteration around the pulleys. Each end of each of the cables is fixed to a controlling device, such as the handle element designated as 30 (for the upper set of pulleys that includes pulley banks 22a and 22b) and 32 (for the lower set of pulleys that includes pulley banks 24a and 24b), so as, in effect, to form an endless cable. Alternatively, as described below, a cord 28 is anchored at one end and wound around each of the pulleys in a series. This configuration may be used to achieve a suitable mechanical advantage and adjustment to accomplish the same degree of adjustment as the endless cable. In this regard, the cable would need to be pulled to twice the length, resulting in excess cord length. Generally, this is not ergonomically desirable, or even feasible, for the great majority of patients. However, as described herein, a take-up element for adjusting a cord length within the closure system when donning or doffing the device is provided.

Figure 5:
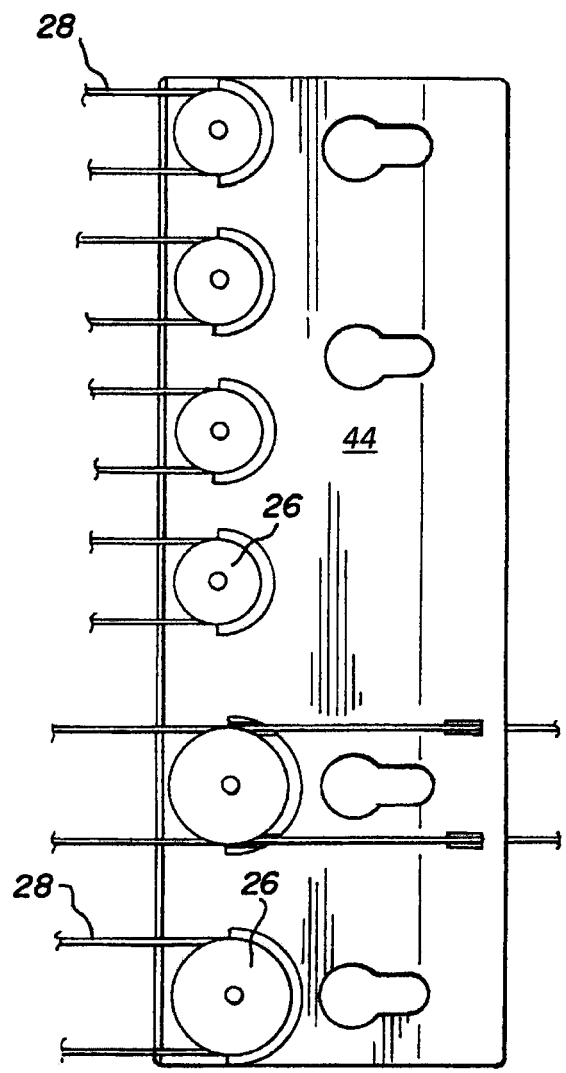
FIG. 5 shows an inner portion of the orthotic device of FIG. 1.

Although the individual pulleys 26 may be secured directly to the material from which the brace body 10 is formed, it is preferred that they are secured to a plate, such as plate 44 illustrated in FIG. 5. The plate is detachably secured to a brace body segment 12a or 12b by any convenient detachable fastening means, such as complementary tabs and slots, hook-and-loop fabric, etc. Each pulley bank 22a, 22b, 24a and 24b includes a cover 48 removably attached to a corresponding plate 44 by any convenient fastener means, such as screws, bolts, recesses and engaging tabs, etc.

As best illustrated in FIG. 2, the ends of each cord 28 are preferably attached to a controlling or handle element for each set of pulleys. The handle element 30, 32 may include an easily graspable member, such as a cloth tab, loop, ring or hail. In the embodiment illustrated in FIG. 2, a bail-shaped member 34, formed from metal or preferably plastic, either rigid or flexible, is secured or formed as part of a tab member 36. The handle 30, 32 may also include a means of detachably securing the handle to a body brace segment after adjustment has been made or the device has been removed from the wearer. Such means of securing could include a series of clasps, a buckle and strap, or a hook-and-loop arrangement. In the closure system shown in FIGS. 1 and 2, a piece of hook-and-loop fabric 38 is affixed to the underside of a portion of the handle, such as the underside of tab member 36. After adjustment has been made and the appropriate tension has been established in each cord 28, the handle 30, 32 may be releasably secured to a segment 12a or 12b by placing the hook-and-loop fabric portion 38 attached to the tab member 36 in contact with a portion of the complementary hook-and-loop fastener 16a on the body brace segment 12a or 12b.

As indicated above, the closure system includes at least two independent pulley banks 22a, 22b, each set mounted on adjacent sides of opposing segments 12a, 12b with a cord 28 running through a corresponding pulley 26 on each adjacent segment 12a, 12b in series and in alteration, such that shortening each cord 28 will pull adjacent inner ends 14c, 14d together and tighten the body brace 12 around the user's torso. As generally shown in FIG. 2 and indicated above, although generally well suited for securing the orthotic device 10 around the user's torso, adjustment of the orthotic device 10, for a number of reasons, may result in a relatively excessive amount of excess cord 28, making placement of the tab member 36 in contact with a portion of the complementary hook-and-loop material 16a on the body brace segment 12a, 12h difficult, cumbersome, or even impossible if proper adjustment of the orthotic device 10 is to be realized and maintained.

Figure 3:
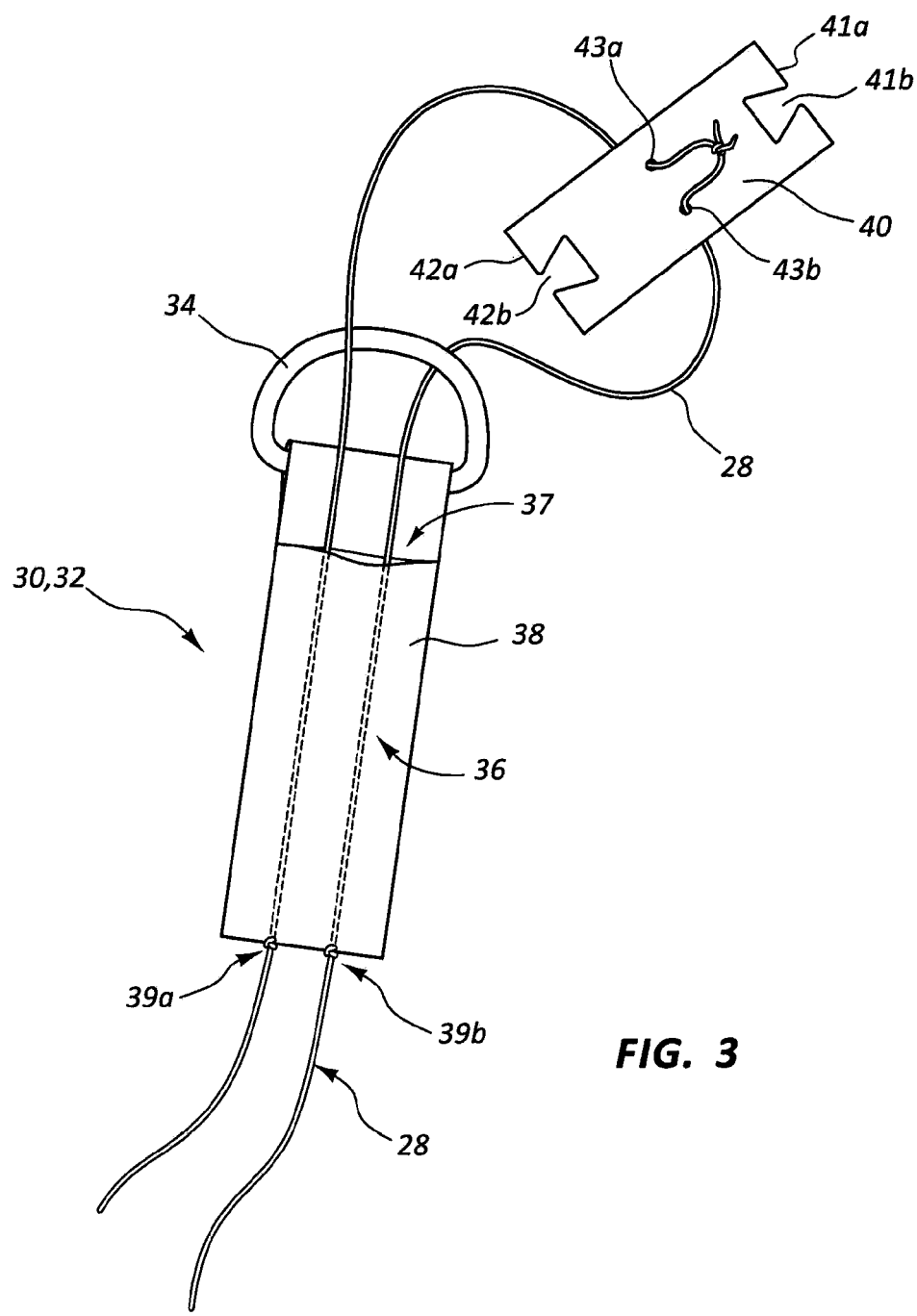
FIG. 3 shows a take-up element for adjusting a cord length within the closure system, with a cord secured thereto extending from a handle element, in accordance with an embodiment of the present invention.

As shown in FIG. 3, to solve the problem of excess cord length, the closure system of the orthotic device 10 further includes a take-up element 40 for adjusting a cord length within the closure system to facilitate placement or the tab member 36 on the complementary hook-and-loop material 16a when donning or doffing the device. In this regard, the take-up element 40 may be of a generally flat elongated shape, and constructed of plastic, metal, or other suitable lightweight and durable material. The take-up element 40 may include a first end 41a having a recessed portion 41b, and a second end 42a, opposite the first end and having a recessed portion 42h. As described below, the recessed portions 41b, 42b are configured to receive or relinquish a predetermined length of cord by having the length of cord wrapped/wound, or unwrapped/unwound, around the take-up element 40 to either shorten or lengthen the cord 28 as desired.

The take-up element 40 may further include a first orifice 43a and a second orifice 43b formed thereon for receiving there-through a cord 28 attached to a corresponding pulley set 20 and its corresponding pulleys 26. Opposite ends of the cord 28 are received through the first and second orifices 43a, 43b, respectively, and tied together to secure the cord 28 to the take-up element 40.

The tab member 36 of the handle element 30, 32 may include a pocket 37 for removably receiving the take-up element 40. The pocket 37 is open at one end for removably receiving the take-up element 40, and is closed to the take-up element 40 and open to the cord 28 at the opposite end. More specifically, the opposite end of the tab member 40 includes openings 39a, 39b that are large enough to permit the ends of the cord 28 to pass through the corresponding openings 39a, 39b while essentially being closed to the take-up element 40.

Figure 4A:
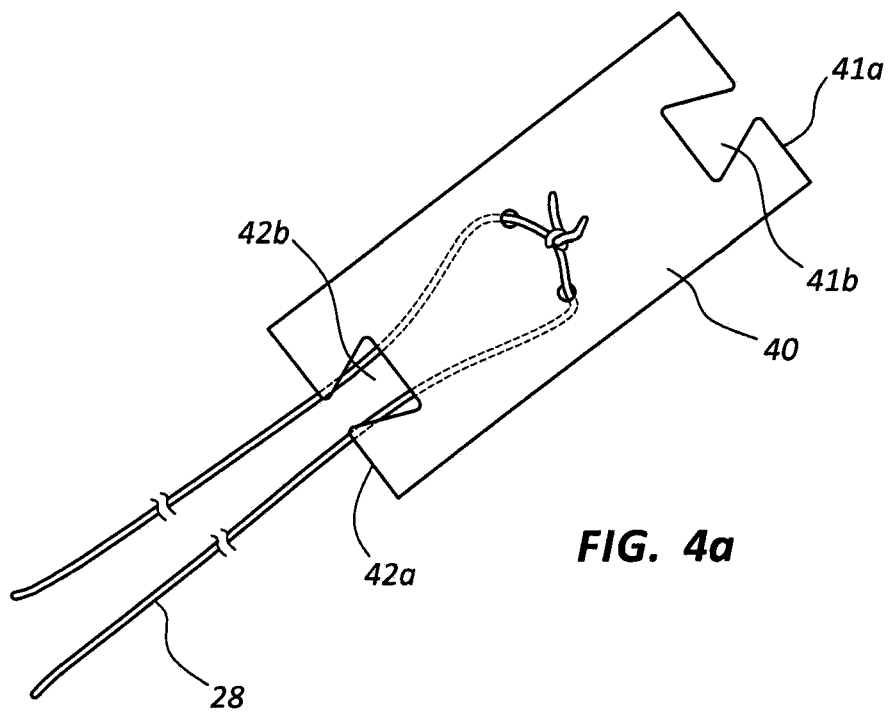
FIG. 4A shows the take-up element of FIG. 3 with a cord secured thereto, in accordance with an embodiment of the present invention.

As shown in FIG. 4A, one process of the closure system for securing the orthotic device 10 around the user's torso includes securing the cord 28 to the take-up element 40 as described above, receiving the take-up element 40 into the pocket 37 of the tab member 36, and pulling the bail shaped member 34 of the handle 30, 32 to pull adjacent inner ends 14c, 14d together and tightening the body brace 12 around the user's torso.

Figure 4B:
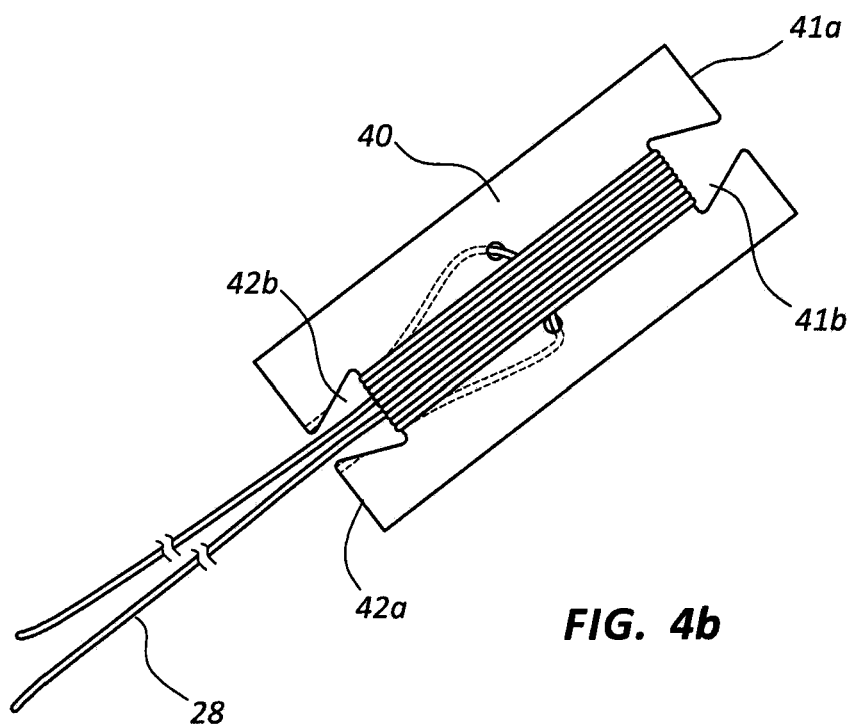
FIG. 4B shows a length of cord wrapped around the take-up element of FIG. 3 to shorten the cord length, in accordance with an embodiment of the present invention.

Alternatively, as shown in FIG. 4B, one process of the closure system for securing the orthotic device 10 around the user's torso includes shortening the cord length to a predetermined length by wrapping the cord 28 around the take-up element 40, receiving the take-up element 40 into pocket 37 of the tab member 36, and pulling the hail shaped member 34 of the handle 30, 32 to pull adjacent inner ends 14c, 14d together and tightening the body brace 12 around the user's torso.

Similarly, one process of the closure system for securing the orthotic device 10 around the user's torso includes lengthening the cord length to a predetermined length by unwrapping the cord 28 from around the take-up element 40, receiving the take-up element 40 into the pocket 37 of the tab member 36, and pulling the bail-shaped member 34 of the handle 30, 32 to pull adjacent inner ends 14c, 14d together and tightening the body brace 12 around the user's torso.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, persons of ordinary skill in the art will recognize that changes may be made in form and detail without departing from the scope of the present disclosure. Thus, the present disclosure is limited only by the claims.

What is claimed is:

1. A closure system for adjusting an orthotic device, the closure system comprising:
   a handle element having a pocket;
   a take-up element configured to be removably received into the pocket; and
   a cord having a length and secured at one end to the take-up element and at an opposite end to the orthotic device to facilitate adjustment of the orthotic device;
   wherein the take-up element is configured to adjust the usable length of the cord.

2. The closure system of claim 1, wherein the take-up element is configured to adjust the usable length of the cord by receiving a segment of the cord.

3. The closure system of claim 2, wherein the take-up element is configured to permit the segment of the cord to be wrapped around the take-up element.

4. The closure system of claim 3, wherein the take-up element includes a first recess and a second recess positioned at opposite ends of the take-up element for securely receiving a wrapped segment of the cord.

5. The closure system of claim 1, wherein:
   the take-up element has a first orifice and a second orifice formed thereon; and
   the cord extends through the first orifice and the second orifice to secure the cord to the take-up element.

6. The closure system of claim 1, wherein:
   the pocket is open at a first end for removably receiving the take-up element and substantially closed at a second end; and
   wherein the second end includes two holes, one sized and configured to permit the cord to enter the pocket, and the other sized and configured to permit the cord to exit the pocket.

7. A method for adjusting an orthotic device, the method comprising the steps of: securing a cord at one end to a take-up element and at an opposite end to the orthotic device to facilitate adjustment of the orthotic device, placing the take-up element into a pocket formed in a handle element attached to the cord, the cord having a length; and adjusting the usable length of the cord using the take-up element.

8. The method of claim 7, wherein the adjusting step includes the step of wrapping a segment of the cord around the take-up element.

9. The method of claim 7, wherein the adjusting step includes the step of unwrapping a segment of the cord from around the take-up element.

10. A closure system for adjusting an orthotic device, the closure system comprising:
   a handle element;
   a take-up element configured to be removably received by the handle element; and
   a cord having a length and secured at one end to the take-up element and at an opposite end to the orthotic device to facilitate adjustment of the orthotic device;
   wherein the take-up element is configured to adjust the usable length of the cord.

11. The closure system of claim 10, wherein the take-up element is configured to adjust the usable length of the cord by receiving a segment of the cord.

12. The closure system of claim 11, wherein the take-up element is configured to permit the segment of the cord to be wrapped around the take-up element.

13. The closure system of claim 12, wherein the take-up element includes a first recess and a second recess positioned at opposite ends of the take-up element for securely receiving a wrapped segment of the cord.

14. The closure system of claim 10, wherein:
   the take-up element has a first orifice and a second orifice formed thereon; and
   the cord extends through the first orifice and the second orifice to secure the cord to the take-up element.

* * * * *